United States Patent
Botich et al.

(12) 
(10) Patent No.: US 6,436,070 B1
(45) Date of Patent: *Aug. 20, 2002

(54) CATHETER INSERTION DEVICE WITH RETRACTABLE NEEDLE

(75) Inventors: Michael J. Botich, Oxnard; Thor R. Halseth, Simi Valley, both of CA (US)

(73) Assignee: MDC Investment Holdings, Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/185,863

(22) Filed: Nov. 4, 1998

Related U.S. Application Data

(63) Continuation-in-part of application No. PCT/US97/22376, filed on Dec. 5, 1997, which is a continuation of application No. 08/847,544, filed on Apr. 23, 1997, now Pat. No. 5,800,395, which is a continuation-in-part of application No. 08/761,088, filed on Dec. 5, 1996, now Pat. No. 6,004,278.
(60) Provisional application No. 60/064,243, filed on Nov. 4, 1997.

(51) Int. Cl.[7] ................................................. A61M 5/00
(52) U.S. Cl. ........................ 604/110; 604/164; 604/195
(58) Field of Search ................................. 604/110, 187, 604/192, 198, 195, 263, 164, 168, 169, 158

(56) References Cited

U.S. PATENT DOCUMENTS

| | | |
|---|---|---|
| 3,123,073 A | 3/1964 | Barr |
| 3,159,159 A | 12/1964 | Cohen |
| 3,306,290 A | 2/1967 | Weltman |
| 3,469,572 A | 9/1969 | Nehring |
| 3,874,367 A | 4/1975 | Ayres |
| 4,150,666 A | 4/1979 | Brush |
| 4,193,399 A | 3/1980 | Robinson |
| 4,307,731 A | 12/1981 | Kaufman |
| 4,418,703 A | 12/1983 | Hoch |
| 4,507,117 A | 3/1985 | Vining |
| 4,588,398 A | 5/1986 | Daugherty |
| 4,642,103 A | 2/1987 | Gettig |
| 4,661,300 A | 4/1987 | Daugherty |
| 4,664,657 A | 5/1987 | Williamitis |
| 4,710,170 A | 12/1987 | Haber |
| 4,747,831 A | 5/1988 | Kulli |
| 4,758,231 A | 7/1988 | Haber |
| 4,774,964 A | 10/1988 | Bonaldo |
| 4,790,827 A | 12/1988 | Haber |
| 4,795,445 A | 1/1989 | Jensen |
| 4,813,426 A | 3/1989 | Haber |
| 4,822,343 A | 4/1989 | Beiser |
| 4,838,863 A | 6/1989 | Allard |
| 4,838,869 A | 6/1989 | Allard |

(List continued on next page.)

*Primary Examiner*—John D. Yasko
(74) *Attorney, Agent, or Firm*—Dann, Dorfman, Herrell and Skillman; Stephen H. Eland

(57) ABSTRACT

A non-reusable needle-bearing safety medical device is provided. The device is operable for inserting an intravenous catheter into a patient. The device includes a needle for piercing the patient's skin and guiding the catheter into the vein of the patient. The needle is operable in two positions, an extended position, in which the needle projects forwardly from a housing, and a retracted position, in which the needle is retracted into the barrel so that the needle is enclosed by the barrel to prevent inadvertent contact with the needle after use. A needle retainer releasably retains the needle in the projecting position against the bias of a spring that biases the needle rearwardly toward the retracted position. After use, the operator displaces an actuator to release the needle. The spring then propels the needle rearwardly into the retracted position. In this way, the device is non-reusable and the needle is shielded to prevent contact with the sharpened tip of the contaminated needle.

10 Claims, 6 Drawing Sheets

U.S. PATENT DOCUMENTS

| | | | |
|---|---|---|---|
| 4,850,374 A | 7/1989 | Diaz-Ramos | |
| 4,850,961 A | 7/1989 | Wanderer | |
| 4,871,355 A | 10/1989 | Kikkawa | |
| 4,892,107 A | 1/1990 | Haber | |
| 4,900,307 A | 2/1990 | Kulli | |
| 4,904,242 A | 2/1990 | Kulli | |
| 4,915,702 A | 4/1990 | Haber | |
| 4,917,101 A | 4/1990 | Horn | |
| 4,927,414 A | 5/1990 | Kulli | |
| 4,944,728 A | 7/1990 | Carrell | |
| 4,947,863 A | 8/1990 | Haber | |
| 4,966,593 A | 10/1990 | Lennox | |
| 4,973,316 A | 11/1990 | Dysarz | |
| 4,978,343 A | 12/1990 | Dysarz | |
| 4,994,034 A | 2/1991 | Botich | |
| 5,000,740 A | 3/1991 | Duchaume | |
| 5,049,133 A | 9/1991 | Villen Pascual | |
| 5,053,010 A | 10/1991 | McGary | |
| 5,064,419 A | 11/1991 | Gaaude | |
| 5,067,490 A | 11/1991 | Haber | |
| 5,070,885 A | 12/1991 | Bonaldo | |
| 5,084,018 A | 1/1992 | Tsao | |
| 5,086,780 A | 2/1992 | Schmitt | |
| 5,092,853 A | 3/1992 | Couvertier, II | |
| 5,102,394 A | 4/1992 | Lasaitis | |
| 5,114,404 A | 5/1992 | Paxton | |
| 5,114,410 A | 5/1992 | Caralt Batlle | |
| 5,125,414 A | 6/1992 | Dysarz | |
| 5,129,884 A * | 7/1992 | Dysarz | 604/164 |
| 5,135,505 A | 8/1992 | Kaufman | |
| 5,167,641 A | 12/1992 | Schmitz | |
| 5,176,650 A | 1/1993 | Haining | |
| 5,180,369 A | 1/1993 | Dysarz | |
| 5,180,370 A | 1/1993 | Gillespie | |
| 5,185,006 A | 2/1993 | Williamitis | |
| 5,188,599 A | 2/1993 | Botich | |
| 5,188,613 A | 2/1993 | Shaw | |
| 5,201,710 A | 4/1993 | Caselli | |
| 5,201,716 A | 4/1993 | Richard | |
| 5,205,829 A | 4/1993 | Lituchy | |
| 5,211,629 A | 5/1993 | Pressly | |
| 5,215,525 A | 6/1993 | Sturman | |
| 5,219,333 A | 6/1993 | Sagstetter | |
| 5,259,392 A | 11/1993 | Schmitt | |
| 5,273,540 A | 12/1993 | Luther | |
| 5,295,974 A | 3/1994 | O'Laughlin | |
| 5,328,482 A | 7/1994 | Sircom | |
| 5,338,305 A | 8/1994 | Plyley | |
| 5,346,480 A | 9/1994 | Hess | |
| 5,376,075 A | 12/1994 | Haughton | |
| 5,385,551 A | 1/1995 | Shaw | |
| 5,389,076 A | 2/1995 | Shaw | |
| 5,395,337 A | 3/1995 | Clemens | |
| 5,407,431 A | 4/1995 | Botich | |
| 5,407,436 A | 4/1995 | Toft | |
| 5,423,758 A | 6/1995 | Shaw | |
| 5,433,712 A | 7/1995 | Stiles | |
| 5,487,732 A | 1/1996 | Jeffrey | |
| 5,487,734 A | 1/1996 | Thorne | |
| 5,496,274 A | 3/1996 | Graves | |
| 5,501,675 A | 3/1996 | Erskine | |
| 5,514,100 A | 5/1996 | Mahurkar | |
| 5,518,004 A | 5/1996 | Schraga | |
| 5,531,713 A | 7/1996 | Mastronardi | |
| 5,545,146 A | 8/1996 | Ishak | |
| 5,562,629 A | 10/1996 | Haughton | |
| 5,562,634 A | 10/1996 | Flumene | |
| 5,573,510 A | 11/1996 | Isaacson | |
| 5,575,777 A | 11/1996 | Cover | |
| 5,579,780 A | 12/1996 | Zadini | |
| 5,584,809 A | 12/1996 | Graba | |
| 5,611,781 A | 3/1997 | Sircom | |
| 5,683,368 A | 11/1997 | Schmidt | |
| 5,685,855 A | 11/1997 | Erskine | |
| 5,685,863 A | 11/1997 | Botich | |
| 5,695,474 A | 12/1997 | Daugherty | |
| 5,697,907 A | 12/1997 | Gaba | |
| 5,704,914 A | 1/1998 | Stocking | |
| 5,800,395 A | 9/1998 | Botich | |
| 5,997,512 A | 12/1999 | Shaw | |
| 6,004,278 A | 12/1999 | Botich | |
| 6,010,486 A | 1/2000 | Carter | |

* cited by examiner

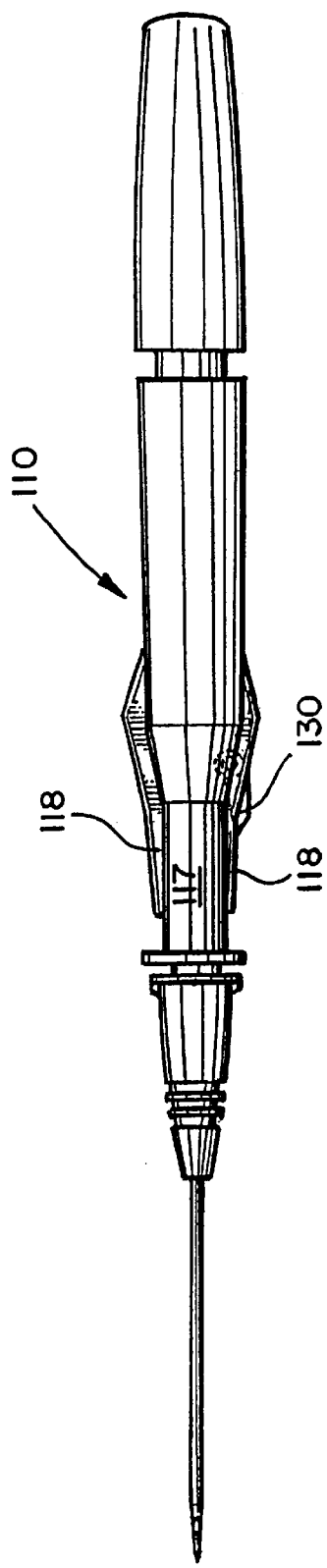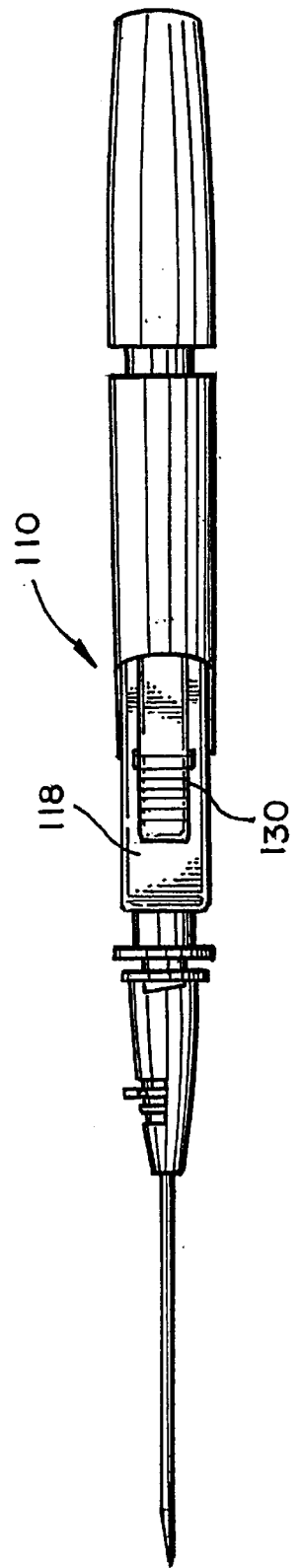

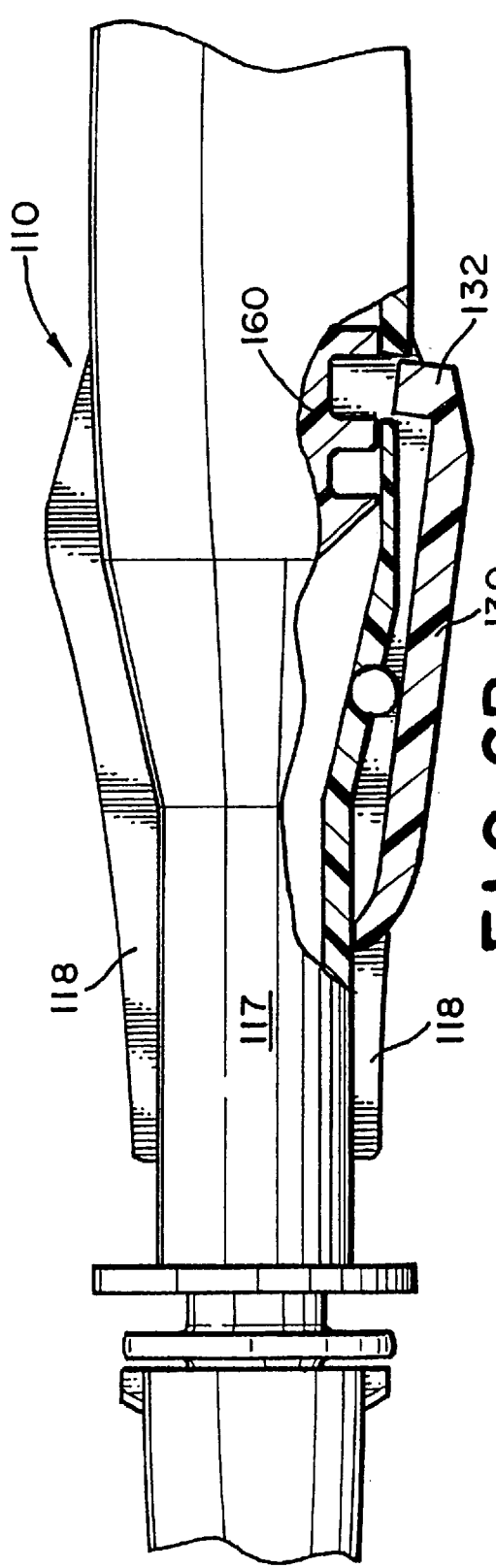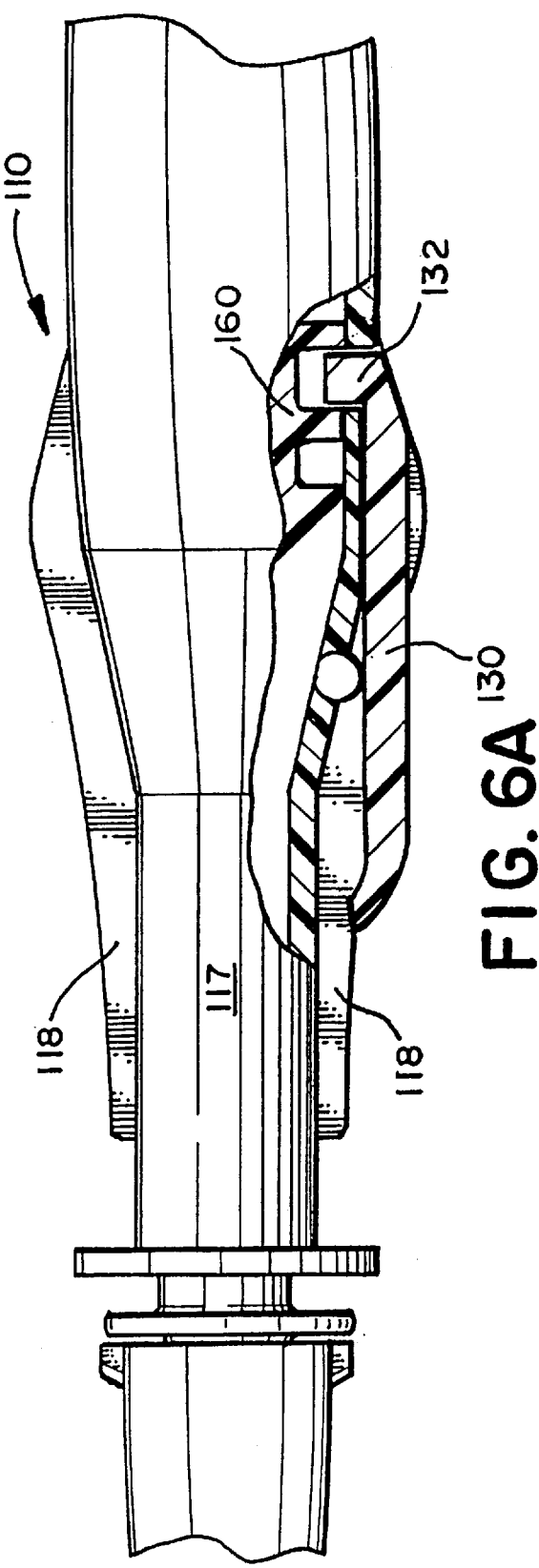

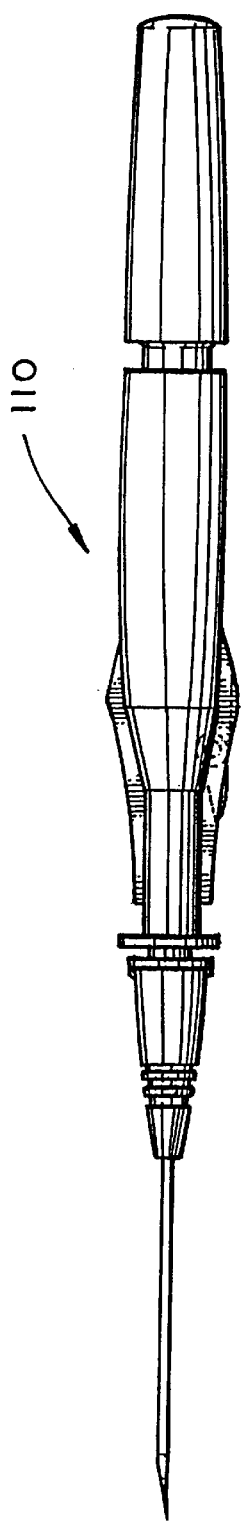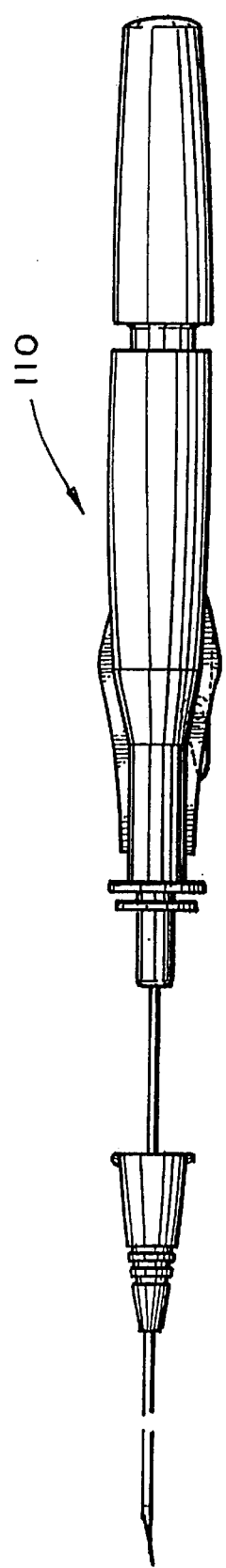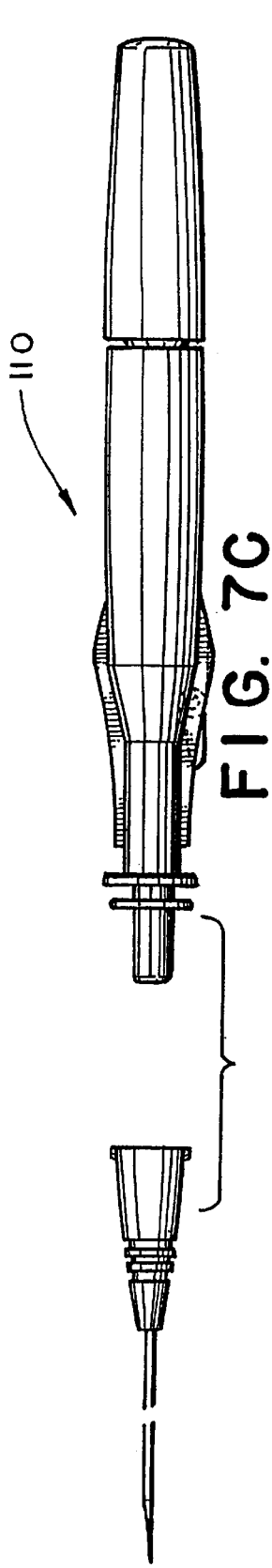

CATHETER INSERTION DEVICE WITH RETRACTABLE NEEDLE

This application is a continuation-in-part of International Patent Application No. PCT/US97/22376, filed Dec. 5, 1997, which is a continuation of U.S. patent application Ser. No. 08/847,544, filed Apr. 23, 1997, now issued as U.S. Pat. No. 5,800,395, which in turn is a continuation-in-part of U.S. patent application Ser. No. 08/761,088, filed Dec. 5, 1996, now U.S. Pat. No. 6,004,278. This application also claims priority to U.S. Provisional Application No. 60/064,243, filed Nov. 4, 1997. Each of the foregoing applications are hereby incorporated herein by reference.

FIELD OF THE INVENTION

The present invention relates to needle-bearing medical devices used, for example, to insert catheters or guide wires into blood vessels of patients or to sample fluid from patients. More specifically, the invention relates to such a device having a retractable needle feature for rendering the device non-reusable and safely disposable.

BACKGROUND OF THE INVENTION

Various types of medical devices employ a needle for piercing the skin of a patient for diagnostic or therapeutic purposes. One such device is an intravenous catheter insertion device, wherein a needle-mounted catheter is positioned within a patient's vein. Once the catheter is properly positioned, the catheter insertion device is withdrawn leaving the catheter in place. Handling of such needle-bearing medical devices after the needle is withdrawn from the patient can result in transmission of various pathogens, most notably human immune virus (HIV), to uninfected medical personnel, due to an inadvertent needle prick.

Since the mid-1980s, concern over the risk of accidental needle stick injuries has spawned a number of design approaches for safety needle devices. Such devices can be broadly categorized as sliding sheath needle devices, wherein a physical barrier is positioned about the needle tip after use, and as needle-retraction devices, wherein the tip of the needle is retracted into the device after use. The category of needle retraction devices can be further subdivided into manual and automatic retraction devices. Manual retraction devices, as exemplified by U.S. Pat. Nos. 4,026,287 to Haller, U.S. Pat. No. 4,592,744 to Jagger, U.S. Pat. No. 4,808,169 to Haber et al. and U.S. Pat. No. 5,067,490 to Haber, require the user to pull or slide a needle-engaging mechanism rearwardly for a sufficient distance to retract the needle into the device. In automatic needle retraction devices, a biasing member, such as a spring, is employed to push or pull the needle into the device in response to activation of some release mechanism by the user. Such devices are exemplified by U.S. Pat. No. 4,813,426 to Haber et al. and U.S. Pat. No. 5,125,414 to Dysarz.

U.S. Pat. No. 4,747,831 assigned to Becton Dickinson and U.S. Pat. No. 4,900,307 to Kulli show respective automatic retractable-needle catheter stylets and syringes. The devices shown in the last-mentioned two patents are disclosed to be actuatable by the user who applies a simple unitary motion that entails a simple single-stage actuation movement in just one direction. Specifically, these latter patents show devices in which retraction is effected by depressing a single surface or member for a short distance in a single direction. Hence, during use of such devices, the user must be mindful not to prematurely trigger the needle retraction mechanism by accidentally contacting the surface for actuating the retraction mechanism. Since medical needle bearing devices are frequently employed under distracting circumstances, it would be desirable to provide an automatic needle retraction mechanism in which a compound action or dual motion is required by the user in order to effect automatic retraction of the needle. Such a mechanism would desirably require the user to act upon more than one surface of the retraction mechanism to effect withdrawal of the needle into the device. It further would be desirable to require that such actions to retract the needle occur along different directional axes to further decrease the likelihood of undesired premature or accidental retraction of the needle.

Of the aforementioned prior art devices which have automatic needle retraction mechanisms, all require a needle structure having an enlarged head, lip or rim extending radially outwardly from the axis of the needle to provide a block or enlarged surface on the needle which is biased toward retraction by the spring and which can be restrained against retraction by a latching arrangement or latch mechanism. In such devices, failure of the latch mechanism can occur to cause premature retraction of the needle. Hence, it would be desirable to provide an automatic needle retraction mechanism in which the latch mechanism operates more directly upon the needle.

After use of a needle bearing medical device, a small volume of contaminated fluid or blood may remain inside the needle after it is withdrawn from the patient. Depending upon the gauge of the needle used with the device, such residual fluid or blood may be ejected from the forward end of the needle during the rearward acceleration experienced in retraction of the needle. Such forward fluid ejection can result from insufficient capillary adhesion to retain the residual fluid against inertial forces during needle retraction, or against the hydraulic force exerted upon the residual fluid by inrushing fluid or air during rearward acceleration in retracting the needle. It would also be desirable to provide a structure in an automatic needle retraction device that would prevent such ejection of residual blood or fluid from the forward end of the needle during retraction.

SUMMARY OF THE INVENTION

In accordance with one aspect of the present invention, there is provided a needle retraction mechanism for a needle bearing medical device wherein a needle retaining member is bonded directly to the needle for selectively holding the needle in a projecting configuration from the device. The needle retaining member has an axial extension configured to provide at least one finger, and preferably a plurality of separable fingers that are joined about a central bore for holding the needle axially within the bore. Mutual engagement between the fingers and the needle can be enhanced by adhesive or thermal bonding. The needle retainer is positioned within the device to restrain the needle against rearward bias exerted upon the needle by a spring. The spring is preferably also bonded directly to the needle, so that neither the bias force or the counteracting restraining force is required to be mediated by any additional structure connected to the needle.

In accordance with another aspect of the present invention, the needle bearing medical device is provided with an automatic retraction mechanism in which the user is required to execute a dual or compound motion in order to actuate the needle for withdrawing the needle into the device by movement of a biasing member. The preferred compound motion requires the user to effect two motions on separate surfaces of the device. Furthermore, these motions are preferably designed to be effected in distinct directions in order to assure intentional needle retraction.

In accordance with another aspect of the present invention, a dual-motion needle retraction mechanism is provided in combination with respective catheter insertion and guide wire insertion devices.

BRIEF DESCRIPTION OF THE DRAWINGS

The foregoing summary as well as the following detailed description of the preferred embodiments of the present invention will be better understood when read in conjunction with the appended drawings, in which:

FIG. 4 is a plan view of an alternate embodiment of a catheter insertion device manifesting aspects of the present invention;

FIG. 5 is a side-elevational view of the catheter insertion device illustrated in FIG. 4;

FIG. 6a is an enlarged fragmentary plan view of the catheter insertion device illustrated in FIG. 4, illustrating the device in a locked position;

FIG. 6b is an enlarged fragmentary plan view of the catheter insertion device illustrated in FIG. 4, illustrating the device in an unlocked position;

FIG. 7a is a plan view of the catheter insertion device illustrated in FIG. 4, illustrating the device prior to use;

FIG. 7b is a plan view of the catheter insertion device illustrated in FIG. 4, illustrating the catheter removed from the device; and FIG. 7c is a plan view of the catheter insertion device illustrated in FIG. 4, illustrating the needle retracted after use.

DETAILED DESCRIPTION OF THE PREFERRED EMBODIMENTS

Figure 1:
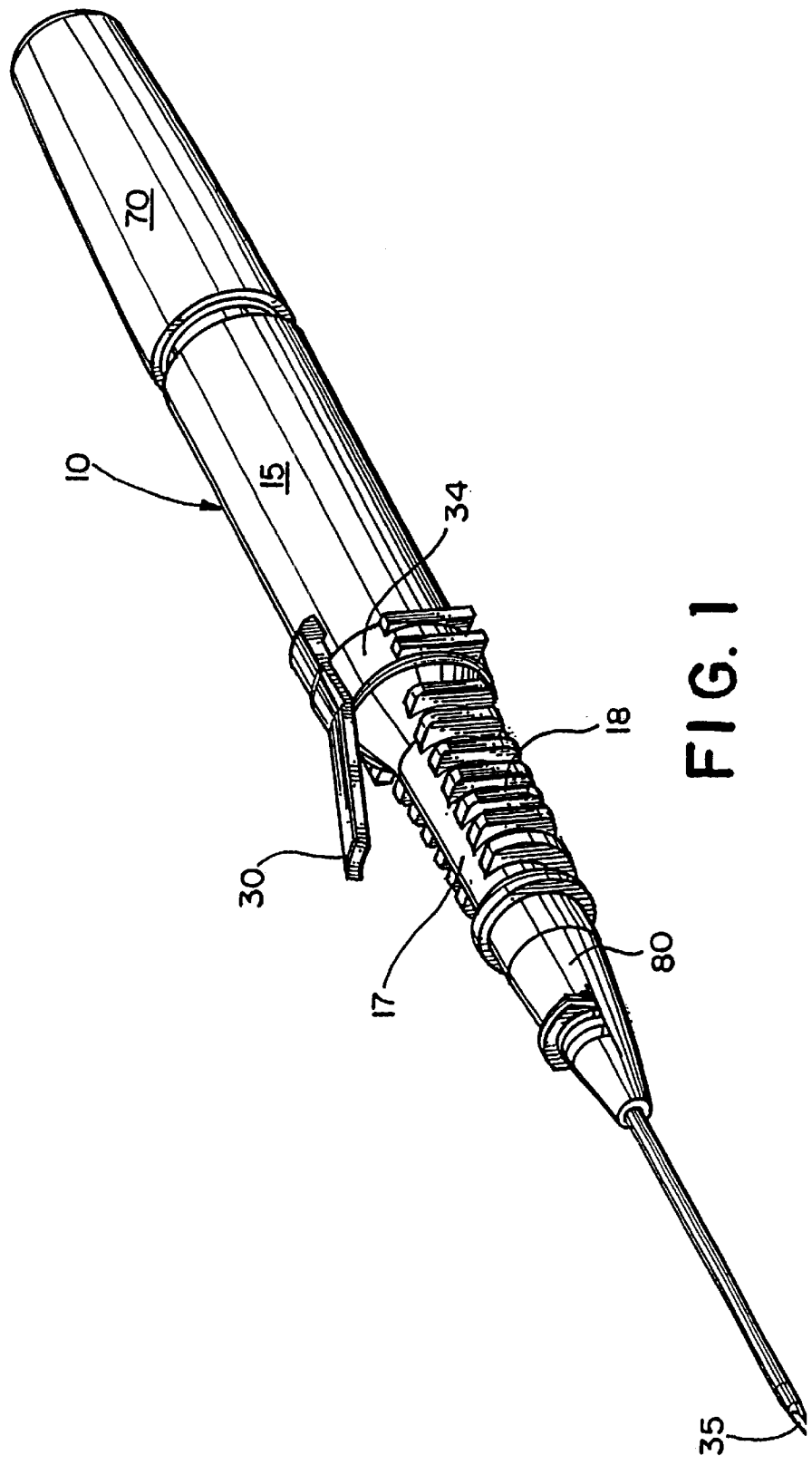
FIG. 1 is a perspective view of a catheter insertion device having a retractable needle, manifesting aspects of the present invention.
Figure 2:
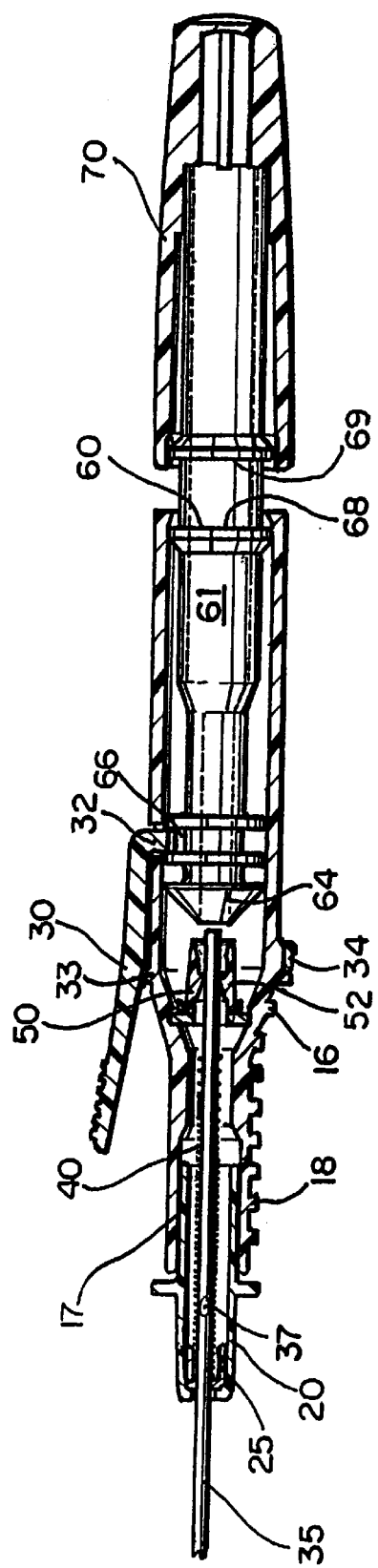
FIG. 2 is a side-elevational view of the catheter insertion device illustrated in FIG. 1.
Figure 3:
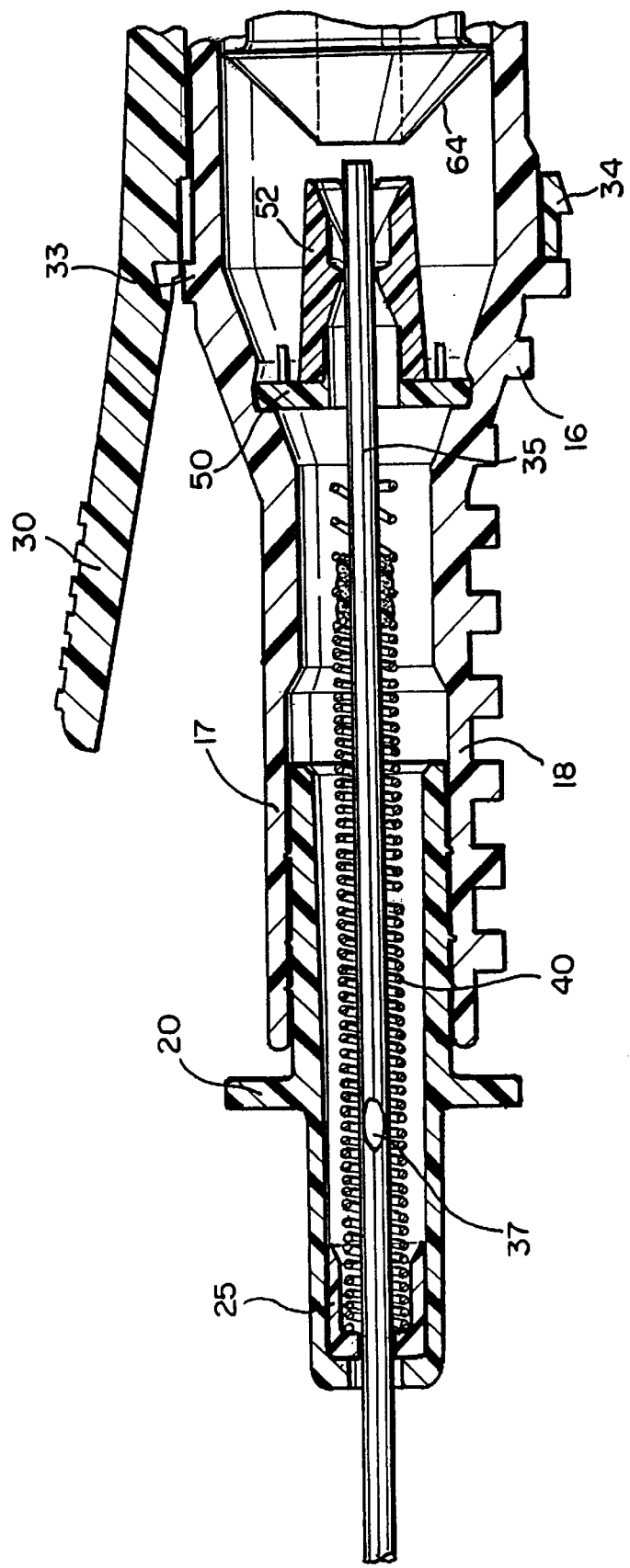
FIG. 3 is an enlarged fragmentary side-elevational view of the catheter insertion device illustrated in FIG. 1.

Referring to the drawings in general, and FIGS. 1–3, in particular, a catheter insertion device 10 having a retractable needle 35 is illustrated. The device is used in connection with inserting a catheter 80 into the vein of a patient. After the catheter is inserted, the insertion needle 35 is retracted into the insertion device 10 so that the needle is beyond the reach of the user.

The catheter insertion device 10 includes a hollow generally cylindrical barrel 15. The rear-end of the barrel 15 is generally opened having a lip that projects radially inwardly. The forward end of the barrel 15 forms a reduced diameter tip 17 having a bore for receiving a cylindrical nose piece 20. The tip 17 includes a gripping portion 18 that is configured to facilitate gripping the device for use. In the present instance, the gripping portion 18 includes a plurality of spaced apart ridges that enable the user to easily grasp the device without slippage. Although the ridges are preferred, the gripping area can be generally smooth if desired.

The needle 35 is operable between an extended position and a retracted position. In the extended position, the needle projects forwardly through an opening in the front end of the nose piece 20 so that the sharpened tip of the needle is exposed. The catheter 80 telescopingly engages the needle 35 and is mounted on the nose piece 20. Preferably, an elastomeric cup-shaped nose seal 25 is disposed in the front end of the nose piece 20 to form a fluid-tight seal between the needle 35 and the opening at the forward end of the nose piece through which the needle projects.

A spring 40 disposed in the nose piece 20 around the needle 35 is bonded to the needle and biases the needle rearwardly toward the retracted position. A needle retainer 50 releasably engages the needle 35 retaining the needle in the extended position. Referring to FIG. 3, the needle retainer 50 includes a plurality of axially elongated circumferentially spaced fingers 52 forming a bore through which the needle 35 passes. The rearward end of the fingers 52 form a rearwardly facing tapered actuation surface. Preferably, the fingers 52 are separated from one another by a plurality of elongated slots that form frangible portions that allow the fingers to be deformed radially outwardly as will be discussed below. Preferably, the needle 35 is bonded directly to the fingers 52 of the needle retainer 50.

Referring again to FIG. 2, a plunger 60 that operates as an actuating member is disposed within the interior of the barrel 15. Preferably the plunger 60 forms a fluid-tight seal with the internal surface of the barrel 15. The forward end of the plunger 60 forms a tapered frustoconical actuation surface that cooperates with the rearward opening of the needle retainer 50. The plunger includes a circumferential annular groove 66 adjacent the actuation surface 64. The annular groove 66 cooperates with a safety latch 30, as will be discussed further below. The plunger 60 also includes a first circumferential flange 68 that cooperates with the lip at the rearward opening of the barrel 15 to prevent the plunger from being removed from the barrel. A rear cap 70 is inserted onto the rear end of the plunger 60. The rear cap 70 has a hollow interior forming a socket for receiving the rearward end of the plunger. A second retention flange 69 on the plunger 60 cooperates with the rear cap 70 to connect the rear cap to the plunger.

The plunger 60 operates to actuate retraction of the needle 35 as follows. Depressing the rear cap 70 axially advances the plunger 60 within the barrel 15 into contact with the rearward end of the needle retainer 50. The forward facing tapered surface 64 of the plunger 60 cooperates with the rearward facing tapered surface of the needle retainer 50. In this way, the plunger operates as a wedge, deforming the fingers 52 radially outwardly, breaking the glue bond between the fingers and the needle 35. Once the needle is released from the needle retainer, the spring 40 projects the needle rearwardly through an opening at the front of the plunger and into a cavity 61 within the plunger. The rear cap 70 has a solid rear surface that acts as a stop, preventing the retracted needle from being projected rearwardly out of the device.

The device 10 includes a safety lever 30 that cooperates with the plunger 60 to prevent the plunger from axially advancing to effect retraction. The safety lever 30 is an elongated lever arm having a latch 32 that cooperates with the annular groove 66 at the forward end of the plunger 60. The lever arm 30 is pivotally mounted on the forward end of the device 10 about a pivot point 33, so that the lever arm is adjacent the gripping portion 18. Preferably, the lever arm 30 overlaps the gripping portion 18 as shown in FIG. 2. The safety lever 30 pivots between a latched position in which the latch 32 engages the plunger 60 and an unlatched position in which the latch is pivoted out of engagement with the plunger. The safety lever is integrally connected with a mounting ring 34 that circumscribes the barrel 15 and abuts a circumferential ridge 16 to retain the safety lever in place at the forward end of the device 10 adjacent the gripping area 18.

To initiate retraction, the user presses the safety lever 30 downwardly to move the latch 32 out of abutment with the annular groove 66 of the plunger 60. While continuing to depress the safety lever 30 into the unlatched position, the user applies pressure to the rear cap 70. This simultaneous dual action drives the plunger 60 forward to effectuate retraction of the needle 35. As can be appreciated, needle retraction thus requires the user to simultaneously apply force to move two parts of the device in respective distinct directions. A variety of structural variations are possible to require such dual action, other than the specific cantilever arm arrangement described herein.

Referring now to FIGS. 4–7c, an alternate catheter insertion device 110 is illustrated. The alternate embodiment 110 is similar to the embodiment 10 illustrated in FIGS. 1–3, except that the alternate embodiment incorporates an alternate safety lever 130. The safety lever 130 pivots about a pivot point 139 on the tip 117 of the device 110. The safety lever 130 overlaps and is incorporated into the gripping portion of the device 110. In this way, the user can depress the safety lever 130 after use of the device 110 without repositioning the user's grip of the device.

Referring to FIGS. 6a–b, the safety lever 130 engages a plunger 160 that is substantially similar to the plunger 60 illustrated in FIGS. 1–3. The safety lever 130 includes a latch 132 that engages the plunger 160 in the latched position as shown in FIG. 6a. Depressing the safety lever 130 pivots the latch 132 out of engagement with the plunger 160 as shown in FIG. 6b. After the safety lever 130 is pivoted out of engagement with the plunger, the end cap of the device 110 can be depressed to axially advance the plunger to effectuate retraction of the needle. As in the embodiment illustrated in FIGS. 1–3, the safety lever and the end cap must be simultaneously depressed in order to effectuate retraction of the needle.

The terms and expressions which have been employed are used as terms of description and not of limitation. There is no intention in the use of such terms and expressions of excluding any equivalents of the features shown and described or portions thereof. It is recognized, however, that various modifications are possible within the scope of the invention as claimed.

That which is claimed is:

1. A catheter insertion device for positioning a catheter in a blood vessel of a patient, the catheter comprising a hub and a cannula connected with the hub, the device comprising:

a barrel having a forward end contoured to mate with an interior surface of the catheter hub, and a gripping portion configured for holding the device during use;

a needle projecting forward from the barrel and having a sharpened tip extending beyond a forward end of the catheter cannula for penetrating the skin of the patient; and a needle retraction mechanism operable by the user to effect retraction of the needle into the barrel after use; the needle retraction mechanism comprising:

a spring for exerting a rearward bias upon the needle;

a needle retainer for releasably holding the needle in the projecting orientation against the bias of the spring;

an actuating member positioned axially within the barrel and movable therein for releasing the needle retainer from holding the needle, the actuating member having a first actuation surface operable for effecting movement of the actuating member;

a stop preventing movement of the actuating member, the stop having a second actuation surface operable to allow movement of the actuating member, the second actuation surface overlapping the gripping portion, whereby operation of the first and second actuation surfaces is required to effect retraction of the needle into the barrel.

2. A medical device, comprising:

a hollow housing;

a needle having a sharpened tip operable between a projecting position in which the sharpened tip projects forwardly from the housing and a retracted position in which the sharpened tip is enclosed within the housing;

a biasing element biasing the needle toward the retracted position; and an arm pivotable radially, and having a manually engageable surface external of the housing, wherein the arm controls actuation of the device preventing the needle from being displaced into the retracted position, and displacement of the arm radially inwardly allows the needle to be displaced into the retracted position.

3. The device of claim 2 comprising a catheter having a catheter hub, and a cannula, wherein the arm is external of the catheter hub.

4. The device of claim 2 wherein the biasing element comprises a spring circumscribing the needle.

5. The device of claim 2 comprising a needle retainer releasably retaining the needle against the bias of the spring.

6. The device of claim 5 comprising an actuator cooperable with the needle retainer to release the needle.

7. The device of claim 6 wherein the arm controls operation of the actuator.

8. The device of claim 2 wherein the arm comprises a latch operable to project through an opening in the housing.

9. The device of claim 2 wherein the housing comprises a gripping area for gripping the housing, and the manually engageable surface of the arm is disposed adjacent the gripping area.

10. The device of claim 2 wherein the arm is biased radially.

\* \* \* \* \*